US012605182B2

(12) United States Patent
Yue et al.

(10) Patent No.: US 12,605,182 B2
(45) Date of Patent: Apr. 21, 2026

(54) ROTATIONAL ATHERECTOMY DEVICE AND MEDICAL DEVICE COMPRISING ROTATIONAL ATHERECTOMY DEVICE

(71) Applicant: SHANGHAI MICROPORT RHYTHM MEDTECH CO., LTD., Shanghai (CN)

(72) Inventors: Bin Yue, Shanghai (CN); Xiaofei Ji, Shanghai (CN); Shiche Sun, Shanghai (CN); Yingzhong Yao, Shanghai (CN)

(73) Assignee: SHANGHAI MICROPORT RHYTHM MEDTECH CO., LTD., Shanghai (CN)

( * ) Notice: Subject to any disclaimer, the term of this patent is extended or adjusted under 35 U.S.C. 154(b) by 503 days.

(21) Appl. No.: 17/637,390

(22) PCT Filed: Aug. 20, 2020

(86) PCT No.: PCT/CN2020/110133
§ 371 (c)(1),
(2) Date: Feb. 22, 2022

(87) PCT Pub. No.: WO2021/032141
PCT Pub. Date: Feb. 25, 2021

(65) Prior Publication Data
US 2022/0313306 A1 Oct. 6, 2022

(30) Foreign Application Priority Data
Aug. 20, 2019 (CN) ......................... 201910769429.X

(51) Int. Cl.
*A61B 17/3207* (2006.01)
*A61B 17/32* (2006.01)

(52) U.S. Cl.
CPC ................ *A61B 17/320758* (2013.01); *A61B 17/32002* (2013.01); *A61B 17/320725* (2013.01);
(Continued)

(58) Field of Classification Search
CPC ...... A61B 17/320758; A61B 17/32002; A61B 17/320725; A61B 2017/320004;
(Continued)

(56) References Cited

U.S. PATENT DOCUMENTS 6,096,054 A * 8/2000 Wyzgala ........ A61B 17/320758
606/180
2002/0077638 A1 * 6/2002 Kadavy .......... A61B 17/320725
606/159
(Continued)

FOREIGN PATENT DOCUMENTS

CN 102056555 5/2011
CN 102056558 5/2011
(Continued)

OTHER PUBLICATIONS

International Search Report issued for International Patent Application No. PCT/CN2020/110133, Date of mailing: Nov. 17, 2020, 10 pages including English translation.
(Continued)

*Primary Examiner* — Tan-Uyen T Ho
*Assistant Examiner* — Bridget E. Rabaglia
(74) *Attorney, Agent, or Firm* — HSML P.C.

(57) ABSTRACT

The present disclosure relates to a rotational atherectomy device and a medical device including the rotational atherectomy device. The rotational atherectomy device includes a drive shaft and a rotational atherectomy component connected to the drive shaft. The rotational atherectomy component includes a base and a rotational atherectomy block.
(Continued)

The rotational atherectomy block is relatively movably assembled on the base. When the rotational atherectomy component rotates, the rotational atherectomy block moves in a direction away from the base.

4 Claims, 6 Drawing Sheets

(52) U.S. Cl.
CPC ............. *A61B 2017/320004* (2013.01); *A61B 2017/320766* (2013.01)

(58) Field of Classification Search
CPC .... A61B 2017/320766; A61B 17/3207; A61B 2017/320741; A61B 17/320783; A61B 2017/320775; A61B 17/22; A61B 2017/320791; A61B 2017/003; A61B 2017/320733; A61B 2017/320032; A61B 2017/22001; A61B 2017/320008; A61B 2017/00309; A61B 2017/00292; A61B 8/12; A61B 17/320016
USPC ........................................................ 606/159
See application file for complete search history.

(56) References Cited

U.S. PATENT DOCUMENTS

| | | | |
|---|---|---|---|
| 2008/0228208 A1* | 9/2008 | Wulfman | A61B 5/415 606/159 |
| 2018/0235652 A1 | 8/2018 | Benjamin et al. | |

FOREIGN PATENT DOCUMENTS

| | | |
|---|---|---|
| CN | 107106204 | 8/2017 |
| CN | 108882947 | 11/2018 |
| CN | 111012448 | 4/2020 |
| CN | 211749912 U | 10/2020 |
| EP | 3141201 | 3/2017 |
| WO | 9944513 A2 | 9/1999 |
| WO | 0176680 A1 | 10/2001 |
| WO | 2009148805 A1 | 12/2009 |
| WO | 2010002507 A1 | 1/2010 |
| WO | 2016108860 A1 | 7/2016 |
| WO | 2017165013 A1 | 9/2017 |
| WO | 2018017525 | 1/2018 |
| WO | 2018156771 | 8/2018 |
| WO | 2018160741 | 9/2018 |

OTHER PUBLICATIONS

Written Opinion issued for International Patent Application No. PCT/CN2020/110133, Date of mailing: Nov. 17, 2020, 8 pages including partial English machine translation.

Extended European Search Report issued for European Patent Application No. 20854433.8, dated Jul. 14, 2023, 12 pages.

Office Action issued for Chinese Patent Application No. 201910769429. X, dated Jul. 17, 2024, 6 pages.

* cited by examiner

ROTATIONAL ATHERECTOMY DEVICE AND MEDICAL DEVICE COMPRISING ROTATIONAL ATHERECTOMY DEVICE

CROSS-REFERENCES TO RELATED APPLICATIONS

This application is a national stage of PCT Patent Application No. PCT/CN2020/110133, entitled "ROTATIONAL ATHERECTOMY DEVICE AND MEDICAL DEVICE COMPRISING ROTATIONAL ATHERECTOMY DEVICE", filed on Aug. 20, 2020; which claims priority to Chinese Patent Application No. 201910769429X, entitled "ROTATIONAL ATHERECTOMY DEVICE" and filed with the Chinese Patent Office on Aug. 20, 2019, the entire contents of which are incorporated herein by reference.

TECHNICAL FIELD

The present disclosure relates to the field of medical devices, and in particular, to a rotational atherectomy device and a medical device including the rotational atherectomy device.

BACKGROUND

Atherosclerosis is more common in large and middle arteries, characterized by thickening of walls and narrowing of lumens caused by the formation of fibrous lipid plaques in intimae of the arteries, and mainly distributed in intimae of heart and brain arteries. Atherosclerosis is a cardiovascular disease with the highest mortality rate due to stenosis or even obstruction of a diseased artery lumen, resulting in diseases such as myocardial infarction and cerebral infarction. Atherosclerotic plaques are generally located in vascular systems of coronary or peripheral arteries and may exhibit different characteristics depending on texture of the plaques. At present, an atherosclerotic excision device is generally used for pretreatment of severe calcification lesions in medical practice.

The use of the atherosclerotic excision device for treatment is based on a principle of rotationally grinding vascular lesions at a high speed through a rotational atherectomy device to remove calcified or fibrotic atherosclerotic plaques and unclog vessels blocked by the plaques, so as to obtain enlarged and smooth vascular lumens to facilitate subsequent stent implantation. In interventional treatment of stenosis at vascular openings and bifurcation, as well as eccentric, long segmental and severely scratched stenoses, coronary rotablation has become a widely used means of removing atherosclerotic plaques.

At present, a rotational atherectomy catheter mainly includes a flexible drive shaft and a grinding head carried by a far end of the drive shaft and covered by wear-resistant materials such as diamond particles. The drive shaft drives the grinding head to rotate at a high speed (about 150000-190000 rpm), push forward, contact and grind to remove lesions. The coronary rotablation can be used for the treatment of highly calcified lesions. Rotational atherectomy followed by stent implantation can improve a success rate of interventional treatment and reduce incidence of complications.

However, the current rotational atherectomy head cannot adjust the grinding aperture in the process of unclogging the lesion, and there is a need to frequently replace the rotational atherectomy catheter of different specifications in the treatment of the plaque. Moreover, an outer diameter of the rotational atherectomy head is large, which makes it difficult to pass through narrow blood vessels.

SUMMARY

According to exemplary embodiments of the present disclosure, a rotational atherectomy device and a medical device including the rotational atherectomy device are provided.

In one aspect of the present disclosure, a rotational atherectomy device is provided, wherein the rotational atherectomy device includes a drive shaft and a rotational atherectomy component connected to the drive shaft, the rotational atherectomy component includes a base and a rotational atherectomy block, the rotational atherectomy block is relatively movably assembled on the base, and when the rotational atherectomy component rotates, the rotational atherectomy block moves in a direction away from the base.

Further, a centroid of the rotational atherectomy component does not coincide with the drive shaft.

Further, the base includes a cavity, and the rotational atherectomy block is arranged in the cavity.

Further, the cavity is in a shape narrow at the top and wide at the bottom, and the rotational atherectomy block is in a shape of an arch narrow at the top and wide at the bottom along a radial direction of the drive shaft.

Further, the base includes two cavities arranged symmetrically, two rotational atherectomy blocks are provided, and the two rotational atherectomy blocks are arranged in the two cavities respectively.

Further, the cavity is provided with an opening, and the rotational atherectomy block partially extends out of the opening with rotation of the base.

Further, the rotational atherectomy block is clamped at the opening when moving to maximum displacement with the rotation of the base.

Further, a bottom area of the rotational atherectomy block is greater than an area of the opening.

Further, the rotational atherectomy component includes a connector, the base is connected to the rotational atherectomy block through the connector, and when the rotational atherectomy component rotates, the connector adjusts a distance between the rotational atherectomy block and the base.

Further, the connector is movably connected to the base through a hinge.

Further, the base is provided with a slot, and when the rotational atherectomy component is in a non-rotating state, the connector and/or the rotational atherectomy block are/is located in the slot.

Further, the connector is a spring.

Further, the rotational atherectomy block is in a shape of an arch along a radial direction of the drive shaft.

Further, an abrading layer is arranged on a surface of the rotational atherectomy block.

In another aspect of the present disclosure, a medical device for removing plaques in blood vessels is provided. The medical device includes the rotational atherectomy device described above.

Further, the medical device further includes a power source, the power source being connected to the rotational atherectomy device to drive the rotational atherectomy device to rotate.

In the rotational atherectomy device according to the present disclosure, the rotational atherectomy component is arranged at an end of the drive shaft and configured to grind and remove plagues at lesions. With rotation of the rotational atherectomy component, the rotational atherectomy block can expand outwards and rotate around a rotation axis of the rotational atherectomy component. The rotational atherectomy block is provided with the abrading layer, so as to break and grind away the lesion plaques in contact. As a rotating speed of the rotational atherectomy component changes, a radius of rotation of the rotational atherectomy block under the centrifugal force and external lesions changes, which leads to the formation of centroid deviation and different rotation sizes of the rotational atherectomy component, so that the rotational atherectomy device can continuously expand a grinding area while rotating, automatically adjust the grinding aperture, and finally achieve the removal of lesion plaques in different ranges.

Specific structures of the present disclosure and functions and effects thereof will be described in further detail below with reference to the accompanying drawings.

BRIEF DESCRIPTION OF THE DRAWINGS

In order to more clearly illustrate the technical solutions in the embodiments or the prior art, the accompanying drawings used in the description of the embodiments or the prior art will be briefly introduced below. It is apparent that, the accompanying drawings in the following description are only some embodiments of the present disclosure, and other drawings can be obtained by those of ordinary skill in the art from the provided drawings without creative efforts.

DETAILED DESCRIPTION OF THE EMBODIMENTS

The technical solutions in the embodiment of the present disclosure will be further described fully and completely with reference to the accompanying drawings. However, it is to be noted that the following embodiments are merely some preferred embodiments in the present disclosure and do not involve all embodiments covered by the technical solutions of the present disclosure.

It is to be noted that, in the description of the present disclosure, when one element is referred to as "fixed to" another element, it may be directly disposed on another element or an intermediate element may exist. When one element is considered to be "connected to" another element, it may be directly connected to another element or an intermediate element may co-exist.

Unless defined otherwise, all technical and scientific terms used herein have the same meanings as would generally understood by those skilled in the technical field of the present disclosure. The terms used herein in the specification of the present disclosure are for the purpose of describing specific embodiments only, and are not intended to limit the present disclosure. The term "and/or" used herein includes any and all combinations of one or more related listed items.

Figure 1:
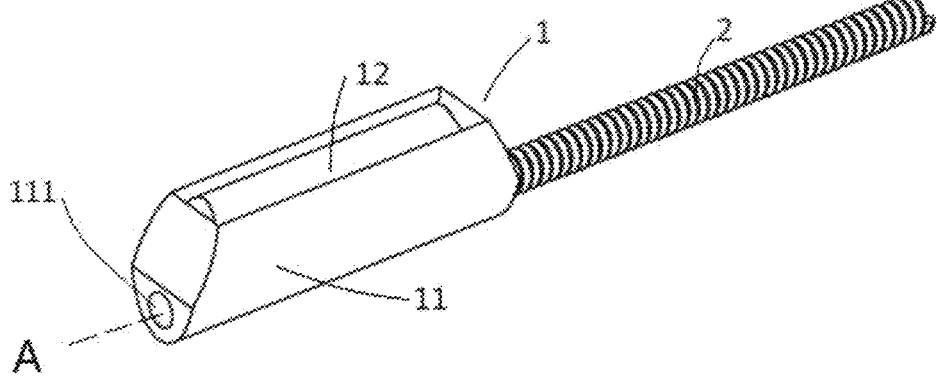
FIG. 1 is a perspective view of a rotational atherectomy device according to Embodiment 1 of the present disclosure in an initial state.

FIG. 1 is a perspective view of a rotational atherectomy device according to Embodiment 1 of the present disclosure in an initial state. A rotational atherectomy component 1 is arranged at an end of a drive shaft 2. The drive shaft 2 is a flexible shaft with an elongated structure, and configured to drive the rotational atherectomy component 1 to rotate. The rotational atherectomy component 1 includes a base 11 and a rotational atherectomy block 12. The base 11 is of an eccentric structure so that a centroid of the rotational atherectomy component 1 does not coincide with the drive shaft 2. The base 11 includes a through hole 111 on one side. The drive shaft 2 can extend into the through hole 111 so as to be integrated with the base 11. The rotational atherectomy block 12 is arranged in a cavity on the other side of the base 11. The cavity is provided with an opening to enable the rotational atherectomy block 12 to move in the cavity. When the drive shaft 2 rotates to drive the rotational atherectomy component 1 to rotate, the rotational atherectomy block 12 is deviated outwards by centrifugal force, moves away from a rotation axis A and rotates around the rotation axis A. The rotation axis A herein refers to a central axis after the drive shaft 2 and the base 11 are sleeved together. When the drive shaft 2 rotates, the rotational atherectomy component 1 can rotate around the rotation axis A.

As the rotating speed of the rotational atherectomy component 1 increases, the centrifugal force on the rotational atherectomy block 12 gradually increases, and the rotational atherectomy block 12 gradually extends to the outside of the cavity, enabling the rotational atherectomy block 12 to contact and grind an external lesion. After removal of a lesion plaque, the resistance on the rotational atherectomy block 12 becomes smaller. Then, after the rotating speed of the rotational atherectomy component 1 is increased, the rotational atherectomy block 12 can further move outwards and contact and grind the lesion until it moves to the maximum displacement and is clamped at the opening of the cavity. Therefore, the rotational atherectomy block 12 can gradually grind the lesion of the contact part and gradually move to the maximum displacement as the rotating speed of the rotational atherectomy component 1 increases, so as to achieve an objective of centroid deviation and an increase in a rotational atherectomy size.

In one preferred embodiment, the rotational atherectomy component 1 is a rotational atherectomy head, and a centroid of the rotational atherectomy component 1 does not coincide with the drive shaft 2. The rotational atherectomy block 12 and the drive shaft 2 are located on two sides of the centroid respectively.

Figure 2:
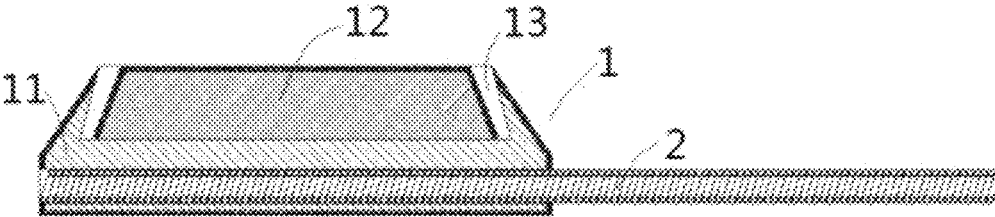
FIG. 2 is a front sectional view of the rotational atherectomy device according to Embodiment 1 of the present disclosure in the initial state.
Figure 3:
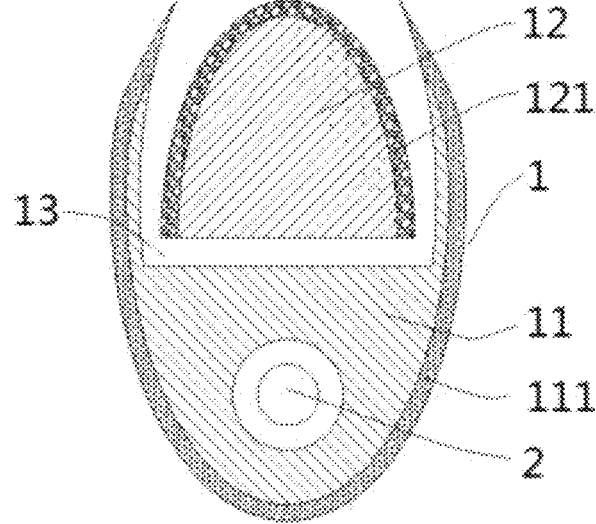
FIG. 3 is a side sectional view of the rotational atherectomy device according to Embodiment 1 of the present disclosure in the initial state.

FIG. 2 and FIG. 3 are a front sectional view and a side sectional view of the rotational atherectomy device according to Embodiment 1 of the present disclosure in the initial state. Referring to FIG. 1 to FIG. 3, the base 11 includes a cavity 13 on the other side. The cavity 13 has an opening at the top, and the rotational atherectomy block 12 is arranged in the cavity 13 and can move in the cavity 13. As shown in FIG. 2, along an axial direction of the drive shaft 2, the cavity 13 has inclined planes at two ends, giving the cavity 13 a shape narrow at the top and wide at the bottom, for example, in a trapezoidal structure narrow at the top and wide at the bottom. Herein, "top" refers to a direction away from the drive shaft, and "bottom" refers to a direction close to the drive shaft 2. As shown in FIG. 3, along a radial direction of the drive shaft 2, two sidewalls of the cavity 13 are arc-shaped. The rotational atherectomy block 12 is arranged in the cavity 13. The rotational atherectomy block 12 has an end which is inclined along the axial direction of the drive shaft 2, and is in a shape of an arch narrow at the top and wide at the bottom along the radial direction of the drive shaft 2., for example, an arch narrow at the top and wide at the bottom. Moreover, a bottom area of the rotational atherectomy block 12 is greater than an area of the opening of the cavity 13, so that the rotational atherectomy block 12 can move along a direction perpendicular to a plane where the opening of the cavity 13 is located and is clamped at the opening when moving to the maximum displacement.

Figure 4:
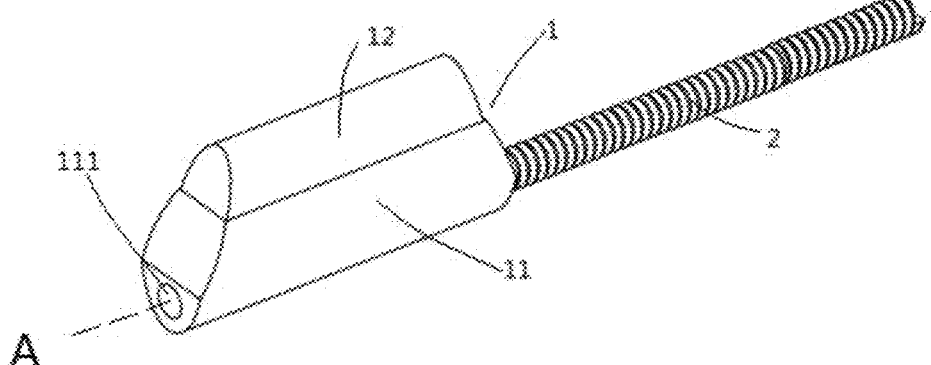
FIG. 4 is a perspective view of the rotational atherectomy device according to Embodiment 1 of the present disclosure in a motion state.
Figure 5:
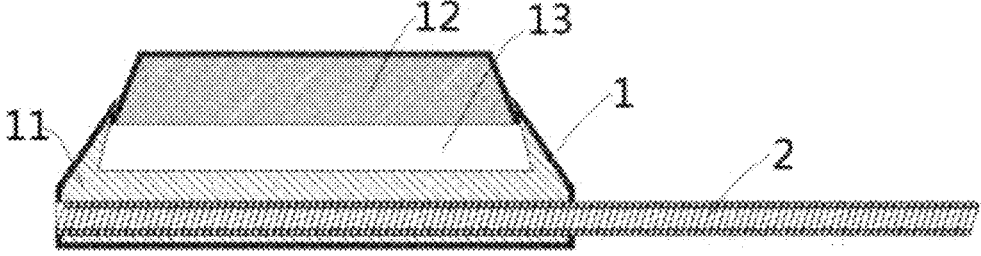
FIG. 5 is a front sectional view of the rotational atherectomy device according to Embodiment 1 of the present disclosure in the motion state.
Figure 6:
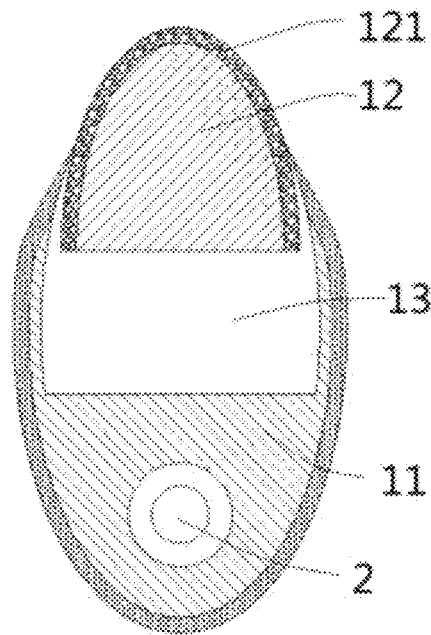
FIG. 6 is a side sectional view of the rotational atherectomy device according to Embodiment 1 of the present disclosure in the motion state.

FIG. 4 to FIG. 6 are schematic diagrams of the rotational atherectomy device according to Embodiment 1 of the present disclosure in a motion state. When the rotational atherectomy component 1 is at a highest speed, the rotational atherectomy block 12 moves to the maximum displacement under the maximum centrifugal force. Limited by the opening of the cavity 13 inside the base 11, the rotational atherectomy block 12 is clamped at the opening and is capable of rotating about the rotation axis A. When the rotational atherectomy component 1 rotates differently from a static state to a maximum speed, the rotational atherectomy block 12 moves in a direction perpendicular to the plane where the opening of the cavity 13 is located under the centrifugal force with different magnitude. At the same time, since the rotational atherectomy component 1 is built into vascular lesions in use, the rotational atherectomy block 12 can grind a lesion in contact when rotating, thereby reducing external resistance. When the lesion in contact with the rotational atherectomy block 12 is ground away, the rotational atherectomy block 12 further extends out of the opening of the cavity 13 under the centrifugal force until it is clamped at the opening, thereby increasing the grinding size of the rotational atherectomy block 12. When the rotational atherectomy component 1 moves to next lesion, the rotational atherectomy block 12 is pressed back to its original state, and then makes preparations for next grinding.

In order to better achieve a grinding effect, an outer surface of the rotational atherectomy block 12 is covered with an abrading layer 121. When the rotational atherectomy component 1 rotates, after the rotational atherectomy block 12 extends out of the cavity 13 under the centrifugal force and contacts the lesion plague, the abrading layer 121 on its surface can act on the lesion plaque, break and wear away the lesion plaque, ablating the lesion plaque. The rotational atherectomy component 1 may rotate at different speeds, so an outward moving distance of the rotational atherectomy block 12 may change during rotation, and lesion plaques at different positions around the rotational atherectomy block 12 may be ground, thereby automatically adjusting the grinding aperture, finally unclogging blood vessels blocked by the plaques, and obtaining an expanded and smooth blood vessel lumen.

Figure 7:
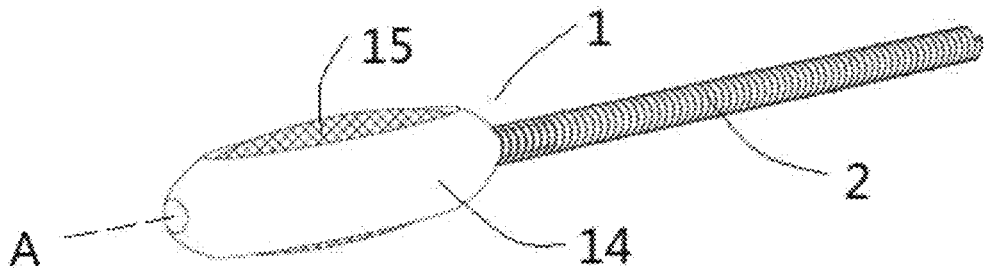
FIG. 7 is a perspective view of a rotational atherectomy device according to Embodiment 2 of the present disclosure in an initial state.
Figure 8:
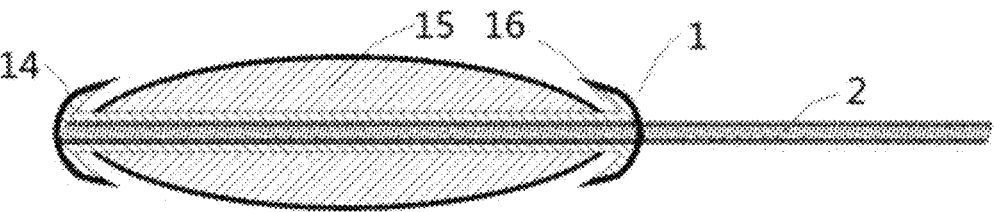
FIG. 8 is a front sectional view of the rotational atherectomy device according to Embodiment 2 of the present disclosure in the initial state.
Figure 9:
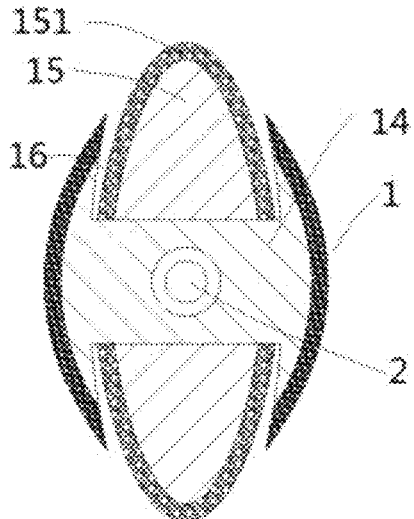
FIG. 9 is a side sectional view of the rotational atherectomy device according to Embodiment 2 of the present disclosure in the initial state.

FIG. 7 to FIG. 9 are schematic diagrams of a rotational atherectomy device according to Embodiment 2 of the present disclosure in an initial state. A rotational atherectomy component 1 is elliptic and spherical, and the rotational atherectomy component 1 sleeves a drive shaft 2 to form a structure with a rotation axis A. The cavities 16 are symmetrically arranged on upper and lower parts of a base 14 (i.e., parts of the base 14 on two sides of the rotation axis A). Two rotational atherectomy blocks 15 are arranged in two cavities 16 respectively, so that, during rotation of the rotational atherectomy component 1, the two rotational atherectomy blocks 15 can be far away from the rotation axis A under the centrifugal force, thereby improving the grinding efficiency.

As shown in FIG. 8, two ends of the cavity 16 along the axial direction of the drive shaft 2 are in a shape of an arc. As shown in FIG. 9, two side surfaces of the cavity 16 long the radial direction of the drive shaft 2 are in a shape of an arc, the rotational atherectomy block 15 corresponding thereto has an arch structure narrower at the top and wider at the bottom, and a bottom area of the rotational atherectomy block 15 is greater than an area of an opening of the cavity 16, so that the rotational atherectomy block 15 can be clamped at the opening when moving to the maximum displacement along a direction perpendicular to a plane where the opening of the cavity 16 is located.

Figure 10:
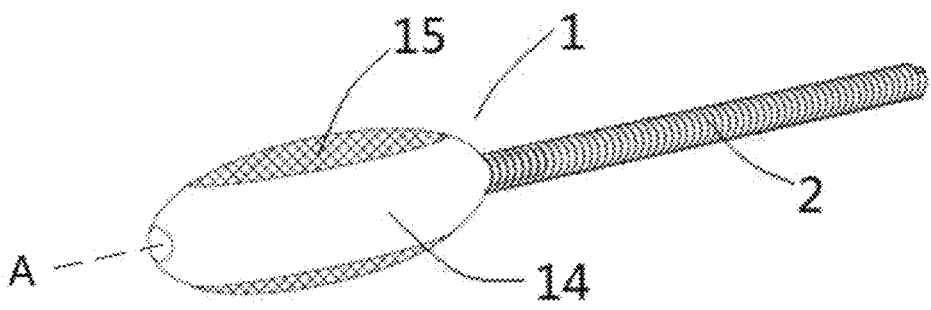
FIG. 10 is a perspective view of the rotational atherectomy device according to Embodiment 2 of the present disclosure in a motion state.
Figure 11:
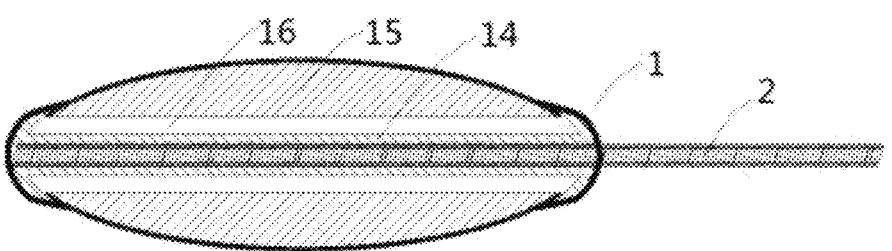
FIG. 11 is a front sectional view of the rotational atherectomy device according to Embodiment 2 of the present disclosure in the motion state.
Figure 12:
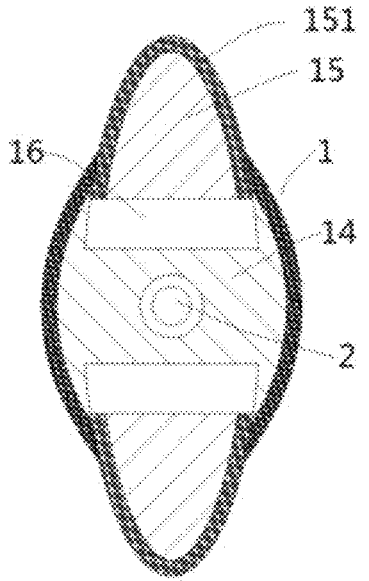
FIG. 12 is a side sectional view of the rotational atherectomy device according to Embodiment 2 of the present disclosure in the motion state.

FIG. 10 to FIG. 12 are schematic diagrams of the rotational atherectomy device according to Embodiment 2 of the present disclosure in a motion state. When the rotational atherectomy component 1 rotates to the maximum speed, the two rotational atherectomy blocks 15 move away from the rotation axis A under the maximum centrifugal force, and are clamped at the openings of the cavities 16 when moving to the maximum displacement. In this case, the rotational atherectomy block 15 can contact the lesion plague to the maximum extent and break and grind the lesion plaque. When the rotational atherectomy component 1 rotates differently between a static state and the maximum speed, outward moving distances of the two rotational atherectomy blocks 15 may change, and lesion plaques at different positions around the rotational atherectomy blocks 15 may be ground, thereby automatically adjusting the grinding aperture, finally unclogging blood vessels blocked by the plaques, and obtaining an expanded and smooth blood vessel lumen.

In addition, an outer surface of the rotational atherectomy block 15 is covered with an abrading layer 151. When the rotational atherectomy component 1 rotates, after the rotational atherectomy block 15 extends out of the cavity 16 under the centrifugal force and contacts the lesion plague, the abrading layer 151 on its surface can act on the lesion plaque, break and wear away the lesion plaque, ablating the lesion plaque.

It is to be noted that the rotational atherectomy blocks according to Embodiment 1 and Embodiment 2 and the corresponding cavity structures are different. The structural principle is that the rotational atherectomy blocks can be stored in the cavities when being static, while the rotational atherectomy blocks can partially extend out of the cavity and be clamped at the openings of the cavities when being dynamic. When the rotating speed decreases, with the decrease of the centrifugal force on the rotational atherectomy blocks, the rotational atherectomy blocks can gradually recover to their initial positions under self-weight or external pressure. Therefore, the embodiments listed in the present disclosure are only a preferred manner and do not imply that all implementations of the present disclosure can be exhausted. Therefore, those skilled in the art can apply other similar cavity structures by simple logical deduction.

Two rotational atherectomy blocks in up-down symmetry are used in Embodiment 2. Compared with one rotational atherectomy block in Embodiment 1, Embodiment 2 has better grinding efficiency, while the eccentric structure in Embodiment 1 has a larger grinding range. Therefore, those skilled in the art may design different combinations applicable to different types of atherosclerotic plaque removal schemes according to actual requirements.

Figure 13:
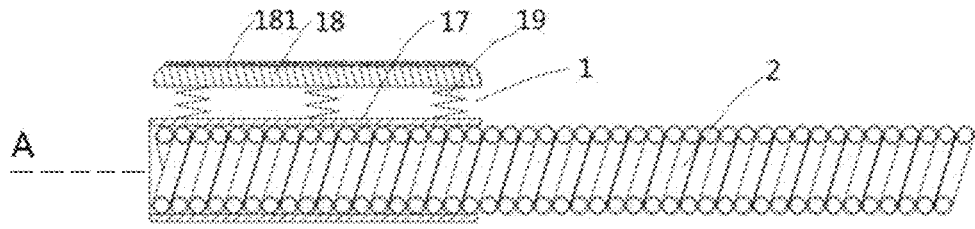
FIG. 13 is a front sectional view of a rotational atherectomy device according to Embodiment 3 of the present disclosure.
Figure 14:
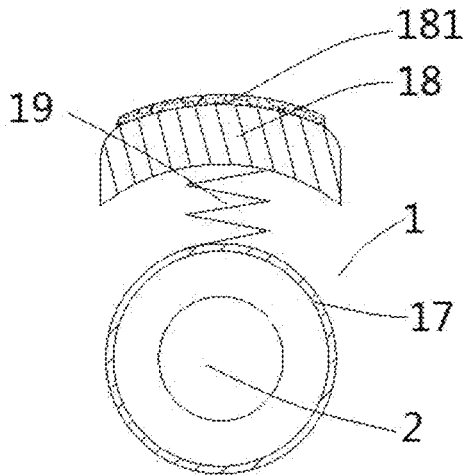
FIG. 14 is a side sectional view of the rotational atherectomy device according to Embodiment 3 of the present disclosure.

FIG. 13 and FIG. 14 are schematic diagrams of a rotational atherectomy device according to Embodiment 3 of the present disclosure. A rotational atherectomy component 1 is arranged at an end of a drive shaft 2. A base 17 is in a shape of a cylinder and sleeves an end of the drive shaft 2. A curved strip rotational atherectomy block 18 is arranged above the base 17 (that is, the rotational atherectomy block 18 is arranged on the base 17 on one side of the drive shaft 2). The rotational atherectomy block 18 is connected to the base 17 by three springs 19. When the drive shaft 2 drives the rotational atherectomy component 1 to rotate, the rotational atherectomy block 18 is driven by the centrifugal force to pull the spring 19 to expand outwards, gradually moving away from the rotation axis A. When the rotating speed gradually decreases, the rotational atherectomy block 18 gradually restores to the initial state under the traction force of the spring 19.

An upper surface (i.e., a surface away from the drive shaft 2) of the rotational atherectomy block 18 is provided with an abrading layer 181. When the rotational atherectomy block 18 rotates, the abrading layer 181 can contact a lesion plague and break and grind the lesion plague, thereby unclogging blocked blood vessels. With the rotational atherectomy device of Embodiment 3, the rotational atherectomy block 18 can rotate in different ranges under the traction of the spring 19, so as to realize a function of automatically adjusting a grinding aperture. In addition, a maximum rotation radius of the rotational atherectomy block 18 is affected by an elastic coefficient of the spring 19. Therefore, the range of the grinding aperture can be further expanded by selecting the spring 19 with different elastic coefficients. Thus, Embodiment 3 has better applicability.

Figure 15:
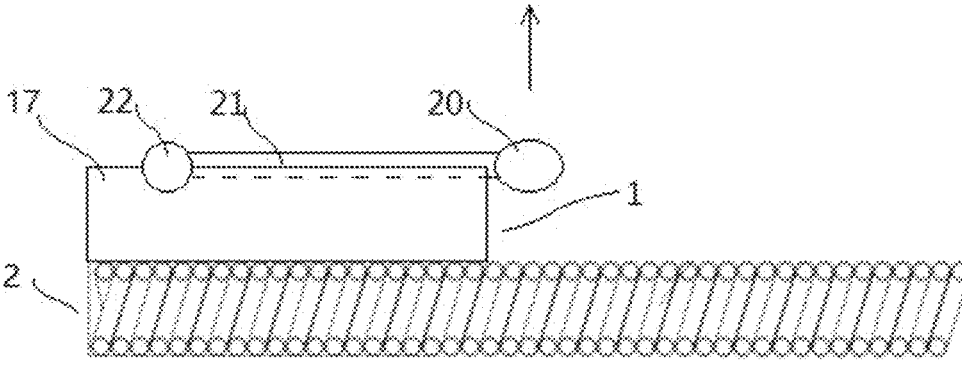
FIG. 15 is a front sectional view of a rotational atherectomy device according to Embodiment 4 of the present disclosure.

FIG. 15 is a front sectional view of a rotational atherectomy device according to Embodiment 4 of the present disclosure. A rotational atherectomy component 1 is arranged at an end of a drive shaft 2. The rotational atherectomy component 1 includes a base 17 and a rotational atherectomy block 20. The rotational atherectomy block 20 is connected to a relatively rigid connecting arm 21. The connecting arm 21 is movably connected to the base 17 through a hinge 22. Preferably, the base 17 is provided with a slot. When the rotational atherectomy component 1 is in a non-rotating state, the connecting arm 21 and/or the rotational atherectomy block 20 may be located in the slot. When the drive shaft 2 drives the rotational atherectomy component 1 to rotate, the rotational atherectomy block 20 moves away from the base 17 due to the centrifugal force. The abrading layer on the rotational atherectomy block 20, when contacting a lesion plague, breaks and grinds the lesion plague, thereby unclogging blocked blood vessels. As the rotating speed of the drive shaft 2 increases, the centrifugal force obtained by the rotational atherectomy block 20 increases synchronously, and a rotation radius of the rotational atherectomy block 20 increases gradually, so as to achieve a purpose of adjusting the grinding aperture and then grinding away lesions in different ranges.

The rotational atherectomy device according to the present disclosure is required to be placed into a living body in use, so materials suitable for the rotational atherectomy component are required to meet requirements of biomedicine. The rotational atherectomy component is made of one or more metal materials, including, but not limited to, stainless steel, nickel, titanium and tungsten. The abrading layer on the surface of the rotational atherectomy block is configured to grind lesion plagues, so its material can enhance wear capability of the rotational atherectomy block, which includes, but is not limited to, one or combinations of diamond, melt quartz, titanium nitride, tungsten carbide and silicon carbide. It is to be noted that the above materials cannot exhaust all the materials involved in the technical solutions according to the present disclosure, and can have same effects as the technical solutions according to the present disclosure. Other types of applicable materials that can be replaced by those skilled in the art through simple analysis are also permitted by the present disclosure, In addition, in order to enable the rotational atherectomy component according to the present disclosure to be better placed into the living body, the other end of the drive shaft is provided with a handheld portion, so as to facilitate medical staff to operate.

In the rotational atherectomy device according to the present disclosure, through different structural designs and material selections for the rotational atherectomy component, on the one hand, the rotational atherectomy block in a static state has a small profile, facilitating the rotational atherectomy component to reach lesions through blood vessels. On the other hand, through the centrifugal force generated under high-speed rotation, an outer diameter profile of the rotational atherectomy block is increased and the centroid is shifted, so as to realize the capability of automatically adjusting the grinding aperture. In the technical solutions according to the present disclosure, the size of the rotational atherectomy component in the static state is reduced, which can thus better reach lesions through blood vessels. The grinding aperture is adjusted by changing the rotating speed of the rotational atherectomy block, thereby reducing the frequency of constantly replacing the rotational atherectomy device in use, enabling simple operation and bringing better economic benefits.

In addition, the present disclosure provides a medical device for removing plaques in blood vessels. The medical device includes the rotational atherectomy device described in the above embodiment. In addition, the medical device further includes a power source. The power source is connected to the rotational atherectomy device to drive the rotational atherectomy device to rotate. In use, the rotational atherectomy device is driven by the power source to rotate, so that the rotational atherectomy block of the rotational atherectomy device can make circumferential movement far away from the rotation axis under the centrifugal force and then grind away the endovascular lesions contacted. Moreover, the rotational atherectomy device can produce different rotation radii according to different driving forces provided by the power source, so as to achieve a purpose of grinding the lesions in different ranges in the blood vessels, thereby reducing the problem of frequent replacement of the rotational atherectomy device in use by an operator and having better market application prospects.

The technical features in the above embodiments may be randomly combined, For concise description, not all possible combinations of the technical features in the above embodiments are described. However, all the combinations of the technical features are to be considered as falling within the scope described in this specification provided that they do not conflict with each other.

The above embodiments only describe several implementations of the present disclosure, which are described specifically and in detail, and therefore cannot be construed as a limitation on the patent scope of the application. It should be pointed out that those of ordinary skill in the art may also make several changes and improvements without departing from the ideas of the present disclosure, all of which fall within the protection scope of the present disclosure. Therefore, the patent protection scope of the present disclosure shall be subject to the appended claims.

What is claimed is:

1. A rotational atherectomy device, comprising a drive shaft and a rotational atherectomy component connected to the drive shaft, the rotational atherectomy component comprises a base and two rotational atherectomy blocks, the two rotational atherectomy blocks being movably assembled on the base, and when the rotational atherectomy component rotates, the two rotational atherectomy blocks move moves in a direction away from the base, wherein the base comprises two cavity cavities formed by walls of the base, the two cavities are arranged symmetrically, and the two rotational atherectomy blocks are arranged in the two cavities, and configured to radially slide within the two cavities respectively, each of the two cavities is provided with an opening, and each of the two rotational atherectomy blocks partially extends out of the opening with rotation of the base, wherein each of the cavities are formed by the walls of the base is in a shape narrow at a top of the respective cavity at the opening and wide at a bottom of the respective cavity, and each of the rotational atherectomy blocks are in a shape of an arch narrow at a top of the respective rotational atherectomy block and wide at a bottom of the respective rotational atherectomy block along a radial direction of the drive shaft; a bottom area of the respective rotational atherectomy block is greater than an area of the respective opening, wherein the top refers to a direction away from the drive shaft, and the bottom refers to a direction close to the drive shaft, wherein the respective cavity and the respective rotational atherectomy block are configured such that the bottom area of the respective rotational atherectomy block is clamped at the opening by the walls at the top of the cavity when moving to a maximum displacement of the respective rotational atherectomy block with respect to the cavity with the rotation of the base, wherein the walls at the top of the respective cavity and a top surface of the respective rotational atherectomy block are configured to engage and wedge the respective rotational atherectomy block at the opening, wherein the base comprises a through hole on one side and the drive shaft can extend into the through hole so as to be integrated with the base.

2. The rotational atherectomy device according to claim 1, wherein an abrading layer is arranged on a surface of each of the rotational atherectomy blocks.

3. A medical device, for removing plaques in blood vessels, wherein the medical device comprises a rotational atherectomy device;

wherein the rotational atherectomy device comprises a drive shaft and a rotational atherectomy component connected to the drive shaft, the rotational atherectomy component comprises a base and two rotational atherectomy blocks, the two rotational atherectomy blocks being movably assembled on the base, and when the rotational atherectomy component rotates, the two rotational atherectomy blocks move meves in a direction away from the base, wherein the base comprises two cavities formed by walls of the base, the two cavities are arranged symmetrically, and the two rotational atherectomy blocks are arranged in the two cavities, and configured to radially slide within the two cavities respectively, each of the two cavities is provided with an opening, and each of the two rotational atherectomy blocks partially extends out of the opening with rotation of the base, wherein each of the cavities are formed by the walls of the base is in a shape narrow at a top of the respective cavity at the opening and wide at a bottom of the respective cavity, and each of the rotational atherectomy blocks are in a shape of an arch narrow at a top of the respective rotational atherectomy block and wide at a bottom of the respective rotational atherectomy block along a radial direction of the drive shaft; a bottom area of the respective rotational atherectomy block is greater than an area of the respective opening; the top refers to a direction away from the drive shaft, and the bottom refers to a direction close to the drive shaft, wherein the respective cavity and the respective rotational atherectomy block are configured such that the bottom area of the respective rotational atherectomy block is clamped at the opening by the walls at the top of the cavity when moving to a maximum displacement of the respective rotational atherectomy block with respect to the cavity with the rotation of the base, wherein the walls at the top of the respective cavity and a top surface of the respective rotational atherectomy block are configured to engage and wedge the respective rotational atherectomy block at the opening;

wherein the base comprises a through hole on one side; the drive shaft can extend into the through hole so as to be integrated with the base.

4. The medical device according to claim 3, wherein the medical device further comprises a power source, the power source being connected to the rotational atherectomy device to drive the rotational atherectomy device to rotate.

* * * * *